United States Patent
Adiga et al.

(10) Patent No.: US 9,017,537 B2
(45) Date of Patent: Apr. 28, 2015

(54) METALLIC AND SEMICONDUCTING CARBON NANOTUBE SORTING

(71) Applicants: Shashishekar P. Adiga, Rochester, NY (US); Hrishikesh V. Panchawagh, San Jose, CA (US); Michael A. Marcus, Honeoye Falls, NY (US)

(72) Inventors: Shashishekar P. Adiga, Rochester, NY (US); Hrishikesh V. Panchawagh, San Jose, CA (US); Michael A. Marcus, Honeoye Falls, NY (US)

(73) Assignee: Eastman Kodak Company, Rochester, NY (US)

( * ) Notice: Subject to any disclaimer, the term of this patent is extended or adjusted under 35 U.S.C. 154(b) by 133 days.

(21) Appl. No.: 13/798,445

(22) Filed: Mar. 13, 2013

(65) Prior Publication Data

US 2014/0262972 A1    Sep. 18, 2014

(51) Int. Cl.
*B03C 5/00* (2006.01)
*G01N 27/447* (2006.01)
*B41J 2/00* (2006.01)
*B41J 2/03* (2006.01)
*B82Y 40/00* (2011.01)

(52) U.S. Cl.
CPC . *B03C 5/00* (2013.01); *B82Y 40/00* (2013.01); *G01N 27/44704* (2013.01); *G01N 27/44743* (2013.01); *B41J 2/00* (2013.01); *B41J 2/03* (2013.01)

(58) Field of Classification Search
CPC ............................................. G01N 27/44743
USPC ................................... 204/547, 643, 600, 450
See application file for complete search history.

(56) References Cited

U.S. PATENT DOCUMENTS

| | | | |
|---|---|---|---|
| 7,161,107 B2 | 1/2007 | Krupke et al. | |
| 7,245,379 B2 * | 7/2007 | Schwabe | 356/436 |
| 8,795,500 B2 * | 8/2014 | Shinoda | 204/600 |
| 2006/0124028 A1 | 6/2006 | Huang et al. | 106/31.92 |
| 2009/0026080 A1 * | 1/2009 | Han et al. | 204/545 |
| 2010/0101983 A1 | 4/2010 | Butler et al. | |
| 2011/0187798 A1 | 8/2011 | Rogers et al. | 347/55 |
| 2013/0108793 A1 | 5/2013 | Sivarajan et al. | 427/372.2 |
| 2013/0194331 A1 | 8/2013 | Katerberg et al. | 347/10 |

FOREIGN PATENT DOCUMENTS

WO    WO 2006075968 A1 *    7/2006    ................ B82B 3/00

OTHER PUBLICATIONS

Kim et al., "Selective Functionalization and Free Solution Electrophoresis of Single-Walled Carbon Nanotubes: Separate Enrichment of Metallic and Semiconducting SWNT", *Chem. Mater.*, vol. 19, No. 7, 2007, pp. 1571-1576.

Komatsu et al., "A Comprehensive Review on Separation Methods and Techniques for Single-Walled Carbon Nanotubes", *Materials*, vol. 3, 2010, pp. 3818-3844.

Lord Rayleigh, "On the Instability of Jets," *Proc. London Math. Soc.* *X* (1878).

* cited by examiner

*Primary Examiner* — Alex Noguerola
(74) *Attorney, Agent, or Firm* — William R. Zimmer (57) ABSTRACT

A method of separating metallic semiconducting carbon nanotubes includes providing a source of a mixture of semiconducting and metallic carbon nanotubes in a carrier liquid with one of the semiconducting and metallic carbon nanotubes being functionalized to carry a charge. The mixture is pressurized to cause a liquid jet of the mixture to be emitted through a nozzle. A drop formation mechanism modulates the liquid jet to form from the jet first and second drops traveling along a path. An electric field modulating device, positioned relative to the jet, produces first and second electric fields. A deflection device applies the first electric field as the first drop is formed to concentrate the functionalized carbon nanotubes in the first drop and applies the second electric field as the second drop is formed. The deflection device causes the first or second drop to begin traveling along another path.

7 Claims, 7 Drawing Sheets

METALLIC AND SEMICONDUCTING CARBON NANOTUBE SORTING

CROSS REFERENCE TO RELATED APPLICATIONS

Reference is made to commonly-assigned, U.S. patent application Ser. No. 13/798,465, entitled "METALLIC AND SEMICONDUCTING CARBON NANOTUBE SORTING", filed concurrently herewith.

FIELD OF THE INVENTION

This invention relates generally to sorting of nanomaterials, and in particularly to separating semiconducting carbon nanotubes and metallic carbon nanotubes.

BACKGROUND OF THE INVENTION

A single-wall carbon nanotube (SWNT) is a cylindrical structure formed by rolling up a graphene sheet. The direction and magnitude of the rolling vector define the chirality and diameter, respectively, of the resulting nanotube and determine whether the nanotube is metallic or semiconducting. Common methods used to synthesize SWNT produce complex mixtures that contain many chiralities. Statistically, one third of the mixture is metallic while the remaining mixture is semiconducting. However, many applications of SWNTs, such as conductive films and high-performance field-effect transistors, require enrichment of nanotubes with metallic and semiconducting properties, respectively. Consequently, there have been intense efforts to develop various sorting techniques for separating SWNTs, including selective chemistry, dielectrophoresis, selective oxidation, ultracentrifugation and DNA wrapping chromatography. Several of these methods have been demonstrated to achieve high-purity separation of metallic and semiconducting SWNTs. However, these methods suffer from problems including low yield or high cost.

Carbon nanotubes have been separated by both physical (electrophoresis and centrifugation) and chemical methods (chromatography, selective solubilization and selective reaction). Electrophoresis has been employed for separating various kinds of SWNTs, synthesized by laser vaporization, arc discharge, chemical vapor deposition (CVD) and HiPco (high pressure CO) process, according mainly to electrical property (metallic/semiconducting) together with length and diameter. Charged biological macromolecules are commonly separated by electrophoresis using gel in an electric field. In order to process SWNTs in the gel, however, the SWNTs have to be individually dispersed with aid of surfactant such as sodium dodecylsulfonate (SDS), sodium cholate (SC) and sodium dodecylbenzenesulfonate (SDBS). This type of metallic/semiconducting separation utilizes different polarizable characters between the nanotubes under an electric field. Dielectrophoresis technique was first used for the alignment and purification of SWNT bundles in isopropyl alcohol and has been extended to separation of individually dispersed SWNTs.

Sodium dodecyl sulphate (SDS) and/or sodium cholate (SC) have been commonly used as detergents to dissolve SWNTs. In 2005, Arnold and Hersam disclosed, in Nature Nanotechnology, 1, 60-65 (2006), an example of density gradient ultracentrifugation (DGU) for separation of the diameter of SWNTs. They used structure discriminating surfactants and applied the DGU to separate metallic/semiconducting nanotubes.

Covalent and non-covalent sidewall chemistries to selectively impart ionic character to metallic or semiconducting carbon nanotubes also have been developed. For example, Woo-Jae Kim et al. disclose in Chemistry of Materials, 19, 1571-1576 (2007), that selective covalent sidewall functionalization of metallic SWNTs can be achieved with p-hydroxybenzene diazonium salt after which a negative charge can be induced on the metallic SWNTs through deprotonation in alkaline solutions, thus enabling subsequent separation by electronic type using free solution electrophoresis.

In US Patent Publication No. 2010/0101983A1, Butler et al. describe a flow sorting method of detecting and separating carbon nanotubes based on a electrophoretic method. In particular, the method involves focusing the dispersion of individually suspended carbon nanotubes into a single file stream in a microfluidic device, and detecting and sorting of metallic and semiconducting nanotubes.

Each of these techniques, however, is disadvantaged in that they are not readily scalable, suffer from low yield, or are expensive. There is clearly a need, therefore, for efficiently sorting semiconducting and metallic nanotubes using a scalable, high yield, or low cost technique.

SUMMARY OF THE INVENTION

According to one aspect of the invention, separation of semiconducting and metallic nanotubes using a continuous inkjet system that includes electrostatic deflection is provided. Ionic side-groups are selectively attached on metallic nanotubes and concentrated in a drop that can be deflected using a deflection electrode of an electrostatic deflection mechanism. The present invention provides a fast and efficient way to sort metallic and semiconducting nanotubes. When compared to conventional techniques, the present invention reduces the need for detection and does not require a single file stream of nanotubes, thus making the present invention more efficient and scalable.

One example embodiment of the present invention provides a system and method for separating metallic SWNTs from semiconducting SWNTs or vice versa to obtain a purified batch of semiconducting SWNTs or metallic SWNTs that has higher yield of the desired product, and is more efficient and scalable when compared to conventions systems and methods. The method includes selectively functionalizing metallic SWNTs with charged functional groups in a mixture containing metallic and semiconducting SWNTs such that the metallic SWNTs carry a net charge and forming a dispersion of this mixture in a fluid such that the metallic and semiconducting SWNTs are suspended in this fluid in a stable dispersion. The metallic SWNTs are enriched by sending the mixture through an inkjet printing system and applying an electric field to selectively attract functionalized metallic SWNTs in a drop. The drop enriched with functionalized metallic SWNTs is the separated from other drops, for example, by deflecting the drop using a deflection mechanism. In another embodiment of the present invention, semiconducting SWNTs are functionalized to have a net charge, are enriched, and then separated from other drops.

According to another aspect of the present invention, a method of separating metallic carbon nanotubes and semiconducting carbon nanotubes includes providing a source of a mixture of semiconducting carbon nanotubes and metallic carbon nanotubes in a carrier liquid with one of the semiconducting carbon nanotubes and metallic carbon nanotubes being functionalized to carry a charge. A nozzle is provided in liquid communication with the source. The source of the mixture is pressurized to a pressure sufficient to cause a liquid jet of the mixture to be emitted through the nozzle. A drop formation mechanism is provided and modulates the liquid jet to cause portions of the liquid jet to break off into a first drop and a second drop with the first drop and the second drop traveling along a path. An electric field modulating device is provided and positioned relative to the liquid jet. The electric field modulating device includes an electrode and a source of time varying electrical potential between the electrode and the liquid jet that produces a first electrical field and a second electric field. A deflection device is provided and applies the first electric field as the first drop is formed to concentrate the functionalized carbon nanotubes in the first drop. The second electric field is applied as the second drop is formed. The first drop is caused to begin traveling along a second path using the deflection device.

BRIEF DESCRIPTION OF THE DRAWINGS

Figure 1:
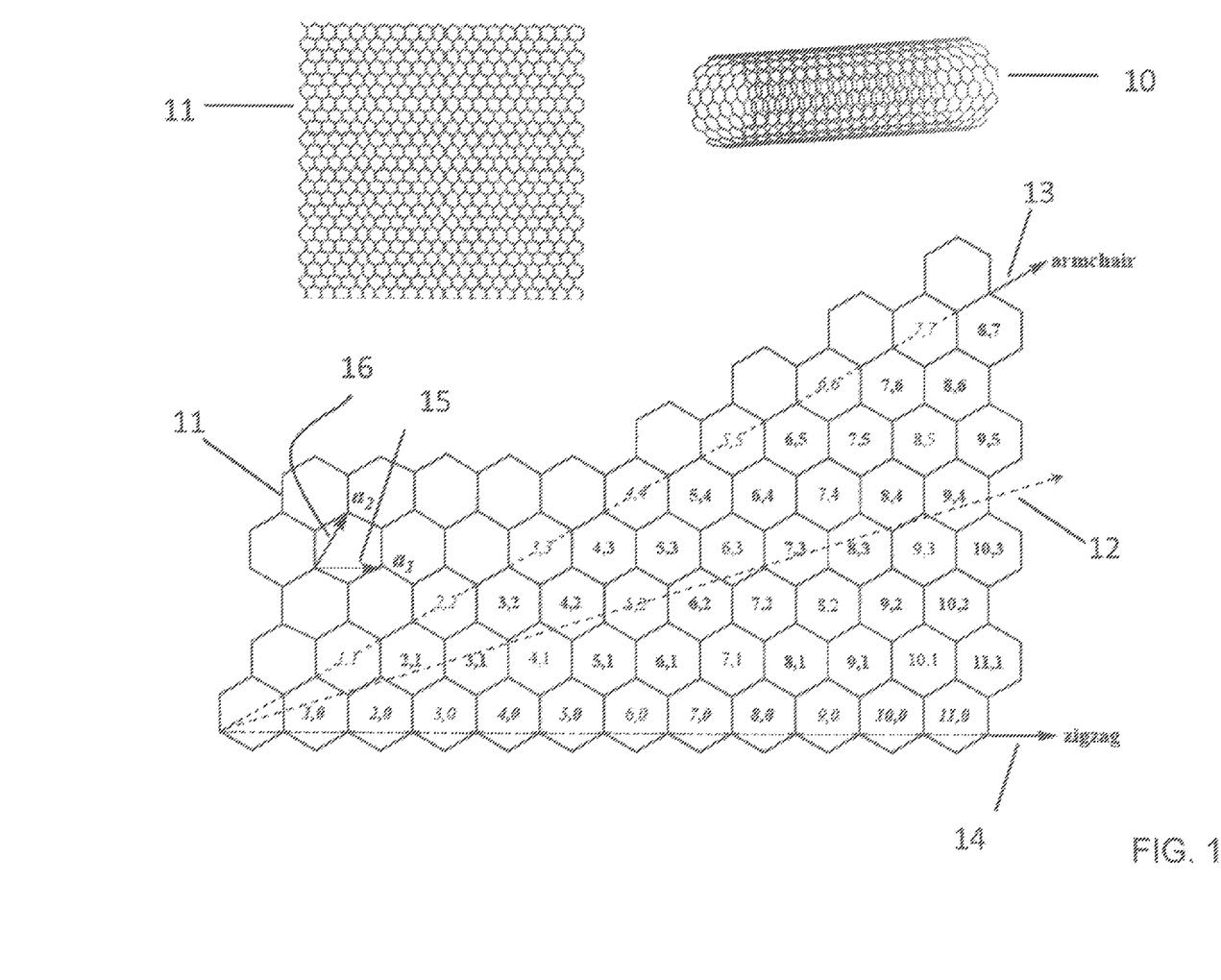

In the detailed description of the preferred embodiments of the invention presented below, reference is made to the accompanying drawings, in which:

FIG. 1 illustrates different ways to roll up a graphene sheet to obtain carbon nanotubes with different chiralities;

FIGS. 2A and 2B illustrate examples of differential functionalization of semiconducting nanotubes and metallic nanotubes, respectively;

FIG. 3 is a block diagram of an example embodiment of a carbon nanotubes separation system of the present invention;

FIG. 4 is a schematic diagram of an example embodiment of the present invention;

FIG. 5 is a schematic diagram of an example embodiment of the present invention showing drops traveling in air after being formed from a liquid jet of a nozzle of a printhead of the present invention;

FIGS. 6A and 6B illustrates jets of a mixture of semiconducting carbon nanotubes and metallic carbon nanotubes in a carrier liquid, with one of the jets, as shown in FIG. 6A, being functionalized to carry a charge without voltage being applied to an adjacent charge electrode, and one of the jets, as shown in FIG. 6B, being functionalized to carry a charge with voltage applied to an adjacent charge electrode; and FIG. 7 is a flowchart outlining the method steps of the present invention.

DETAILED DESCRIPTION OF THE INVENTION

The present description will be directed in particular to elements forming part of, or cooperating more directly with, apparatus in accordance with the present invention. It is to be understood that elements not specifically shown or described may take various forms well known to those skilled in the art. In the following description and drawings, identical reference numerals have been used, where possible, to designate identical elements.

The example embodiments of the present invention are illustrated schematically and not to scale for the sake of clarity. One of the ordinary skills in the art will be able to readily determine the specific size and interconnections of the elements of the example embodiments of the present invention.

Throughout the specification and claims, the following terms take the meanings explicitly associated herein, unless the context clearly dictates otherwise. The meaning of "a," "an," and "the" includes plural reference, the meaning of "in" includes "in" and "on." Additionally, directional terms such as "on", "over", "top", "bottom", "left", "right" are used with reference to the orientation of the Figure(s) being described. Because components of embodiments of the present invention can be positioned in a number of different orientations, the directional terminology is used for purposes of illustration only and is in no way limiting.

As described herein, example embodiments of the present invention provide a printing system, a printhead, a printhead component(s), or printing methods typically used in inkjet printing systems. In such systems, the liquid is an ink for printing on a recording media. The present invention, however, other applications are emerging, which use inkjet print heads to emit liquids (other than inks) that need to be finely metered or deposited with high spatial resolution. The present invention includes an inkjet printing system, printhead, and printhead components to separate semiconducting and metallic nanotubes. As such, as described herein, the terms "liquid" and "ink" refer to any material, for example, semiconducting and metallic nanotubes, that can be ejected by the printing system, printhead, or printhead components of the present invention described below.

Continuous inkjet (CIJ) drop generators rely on the physics of an unconstrained fluid jet, first analyzed in two dimensions by F. R. S. (Lord) Rayleigh, "Instability of Jets," Proc. London Math. Soc. 10 (4), published in 1878. Lord Rayleigh's analysis showed that liquid under pressure, P, will stream out of a hole, the nozzle, forming a liquid jet of diameter $d_j$, moving at a velocity $v_j$. The jet diameter $d_j$ is approximately equal to the effective nozzle diameter $d_n$ and the jet velocity is proportional to the square root of the reservoir pressure P. Rayleigh's analysis showed that the jet will naturally break up into drops of varying sizes based on surface waves that have wavelengths $\lambda$ longer than $\pi d_j$, i.e. $\lambda \geq \pi d_j$. Rayleigh's analysis also showed that particular surface wavelengths would become dominate if initiated at a large enough magnitude, thereby "stimulating" the jet to produce mono-sized drops.

Continuous inkjet (CIJ) drop generators employ a periodic physical process, a so-called "perturbation" or "stimulation" that has the effect of establishing a particular, dominate surface wave on the jet. The stimulation results in the break off of the jet into mono-sized drops synchronized to the fundamental frequency of the perturbation. It has been shown that the maximum efficiency of jet break off occurs at an optimum frequency $F_{opt}$ which results in the shortest time to break off. At the optimum frequency $F_{opt}$ the perturbation wavelength $\lambda$ is approximately equal to $4.54d_j$. The frequency at which the perturbation wavelength $\lambda$ is equal to $\pi d_j$ is called the Rayleigh cutoff frequency $F_R$, since perturbations of the liquid jet at frequencies higher than the cutoff frequency won't grow to cause a drop to be formed. The drop stream that results from applying Rayleigh stimulation will be referred to herein as a stream of drops of predetermined volume.

The example embodiments of the present invention discussed below with reference to FIGS. 1-6 are described using particular combinations of components, for example, particular combinations of drop charging structures, drop deflection structures, drop catching structures, drop formation devices, also called stimulation devices, and drop velocity modulating devices. It should be understood that these combinations of components are interchangeable and that other combinations of these components are within the scope of the invention.

The system of nomenclature for single walled carbon nanotubes (SWNTs) is illustrated in FIG. 1. The structure of single-wall carbon nanotube (SWNT) 10 can be described as atomically thin tubes formed by rolling up a graphene sheet 11. The properties of SWNTs are determined by the alignment of the hexagons with respect to the tube axis. Since a SWNT 10 can be prepared by rolling up a graphene sheet 11 into a seamless cylinder, the structure is defined by a roll-up vector $C_h$ 12 defined by two unit vectors $a_1$ 15 and $a_2$ 16; $C_h=na_1+ma_2$, where n and m are integers and designated as the roll-up index (n, m) as shown in FIG. 1. The (n, m) and $C_h$ have been referred to as—chiral index (or simply—chirality) and—chiral vector, respectively. A roll-up vector with m=0 14 results in zigzag nanotubes and a roll-up vector with n=m 13 gives armchair nanotubes. For their electronic properties, armchair SWNTs have metallic properties, and zigzag and chiral SWNTs are either metallic or semiconducting, depending on the roll-up index (shown in FIG. 1). While armchair and zigzag are achiral, a chiral SWNT has a pair of helical isomers.

Figure 2:
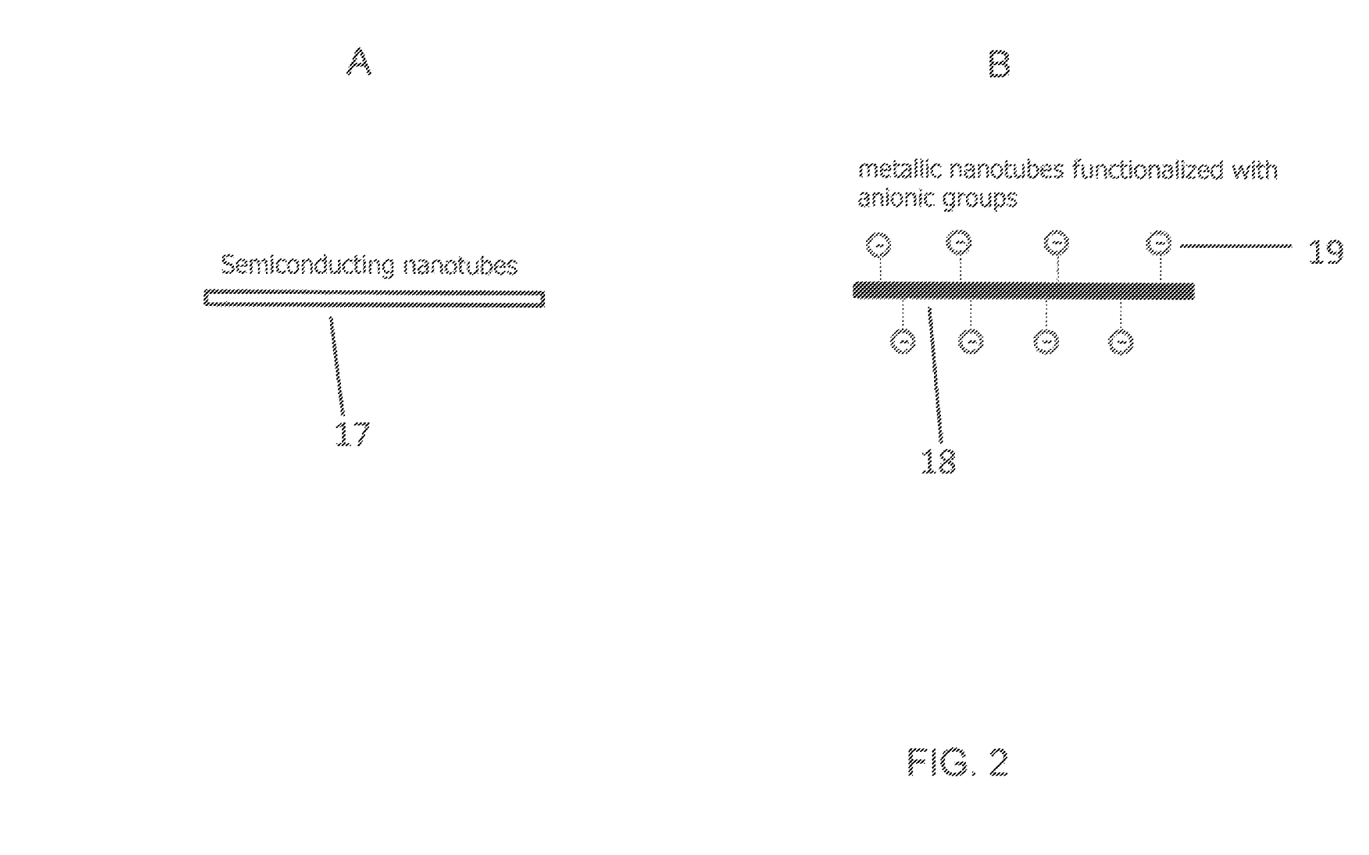

FIG. 2A illustrates an unfunctionalized semiconducting SWNT 17. As shown in FIG. 2B, the metallic SWNT 18 is selectively and covalently functionalized with an anionic group 19. In other example embodiments of the invention, the metallic SWNT can be selectively and non-covalently functionalized with anionic or cationic functional groups or molecules.

Figure 3:
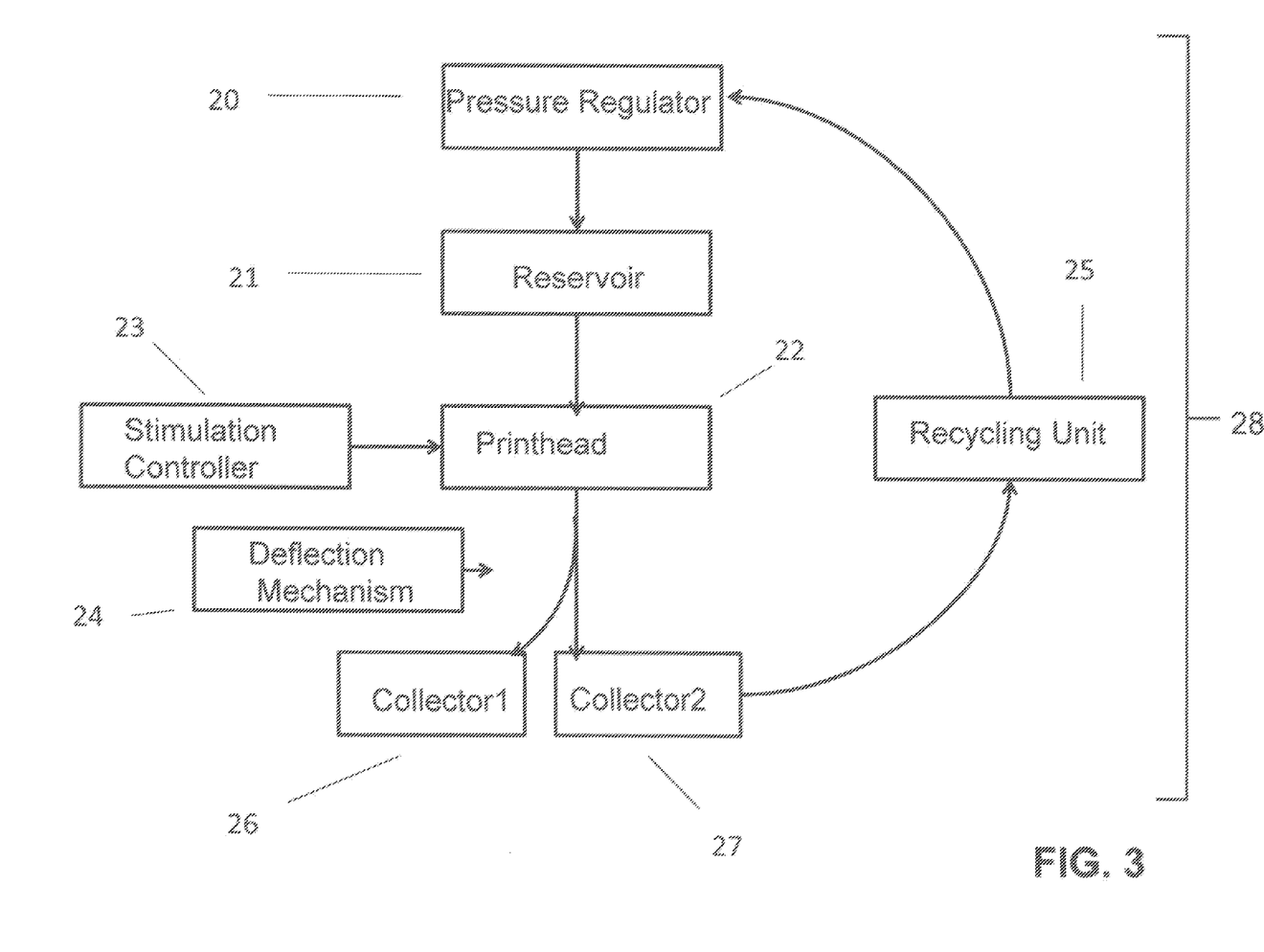
Figure 4:
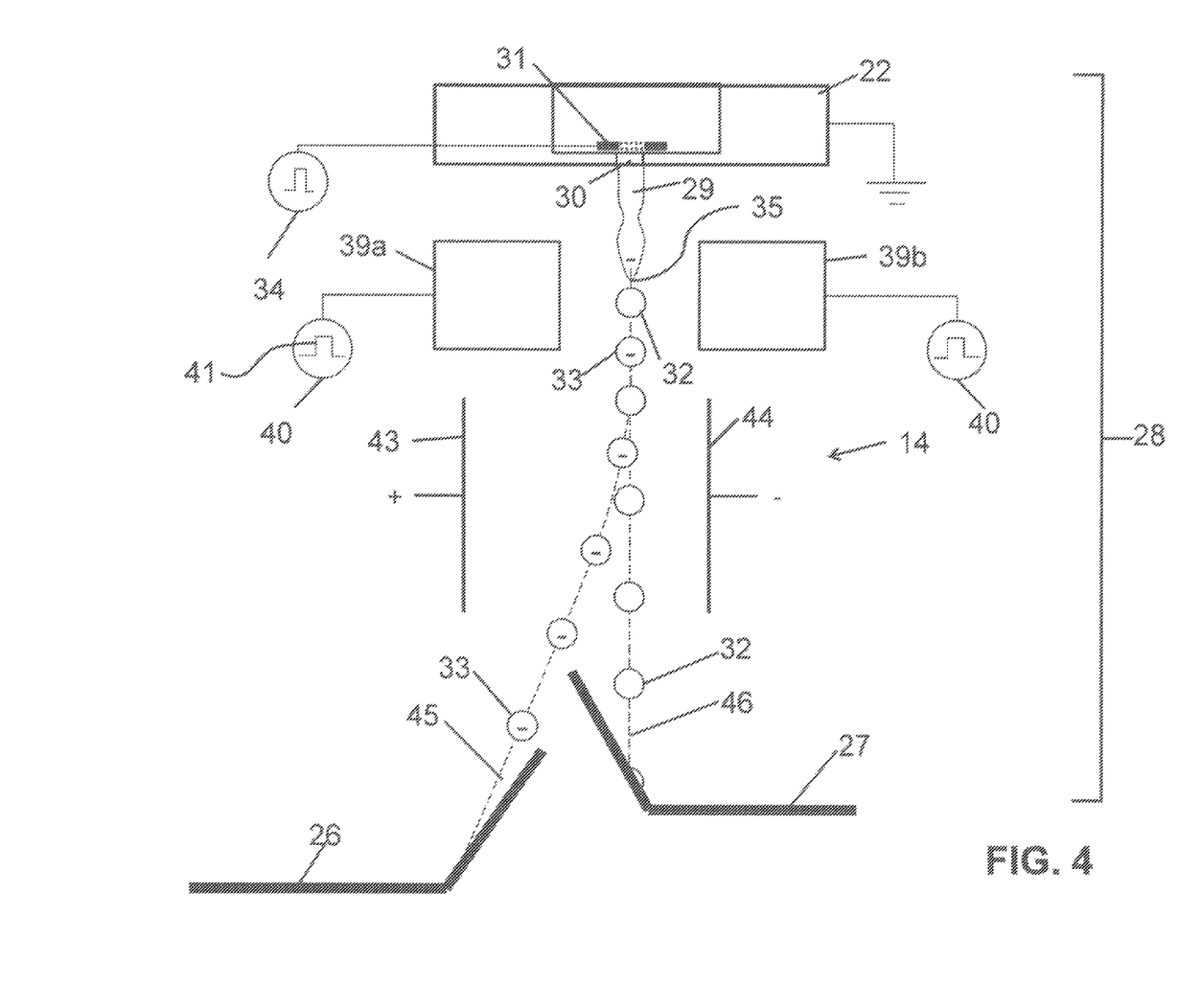
Figure 5:
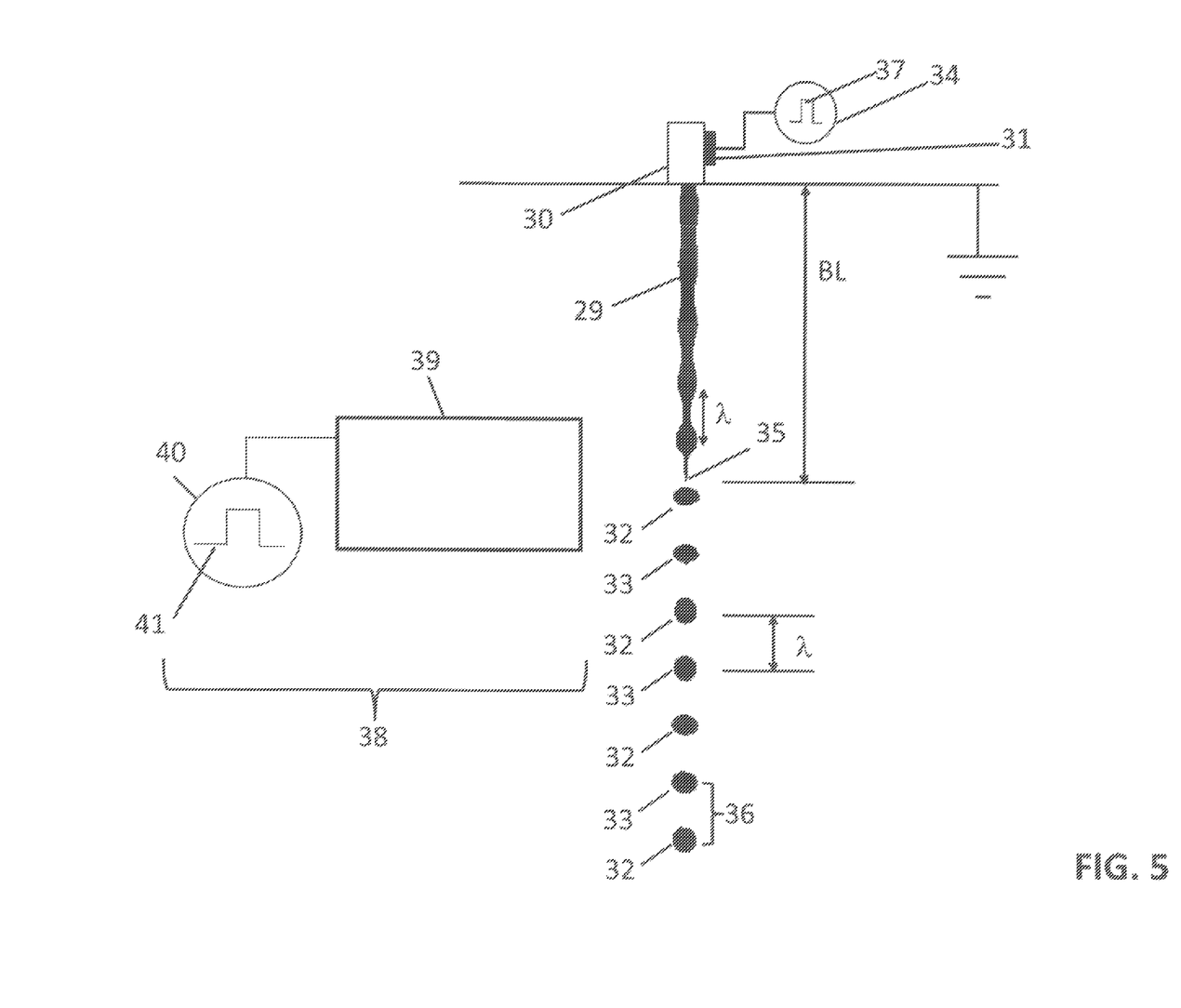

A continuous inkjet printing based SWNT separation system 28 is shown in FIGS. 3, 4 and 5. System 28 includes an ink reservoir 21 that continuously pumps ink into a printhead 22, also called a liquid ejector, to create a continuous stream, also referred to as a jet, of ink 29 from each of the nozzles 30 of the liquid ejector 22. The stimulation controller 23 generates stimulation waveforms 37, patterns of time-varying electrical stimulation pulses, to cause a stream of drops to form from the jet beyond the outlet of each of the nozzles 30 on printhead 22, described in more detail below. These stimulation pulses of the stimulation waveforms 37 are applied to stimulation device(s) 31, for example, a heater or piezoelectric device, associated with each of the nozzles 30 with appropriate amplitudes, and timings to cause drops 32 and 33 to break off from the continuous stream 29. The printhead 22 and deflection mechanism 24 work cooperatively in order to determine whether ink droplets are deflected to a first collector 26, collector 1, or deflected to a second collector 27, collector 2, and recycled via the ink recycling unit 25. The ink in the ink recycling unit 25 is typically directed back into the ink reservoir 21. In other example embodiments of the invention, one or both of first collector 26 and second collector 27 can be replaced with a receiver upon which either of drops 33 or drops 32, respectively, impinge or contact.

The ink is distributed under pressure to the back of the printhead 22 by an ink channel that includes a chamber or plenum formed in a substrate, for example, a silicon substrate. Alternatively, the chamber could be formed in a manifold piece to which a silicon substrate nozzle plate is attached. The ink preferably flows from the chamber through slots or holes etched through the silicon substrate of the printhead 22 to its front surface, where a plurality of nozzles and stimulation devices are situated. The ink pressure suitable for optimal operation will depend on a number of factors, including geometry and thermal properties of the nozzles and thermal and fluid dynamic properties of the ink. The constant ink pressure can be achieved by applying pressure to ink reservoir 21 under the control of ink pressure regulator 20. A deflection mechanism 24 includes electrostatic deflection components, described in more detail below.

The stimulation controller 23 includes one or more stimulation waveform sources 34 that generate drop formation waveforms 37 in response to the input data and provide or apply the drop formation waveforms 37, also called stimulation waveforms, to the drop formation device(s) 31 associated with each nozzle 30 or liquid jet 29. In response to the energy pulses of applied stimulation waveforms 37, the drop formation device 31 perturbs the continuous liquid stream 29, also called a liquid jet 29, to cause individual liquid drops to break off from the liquid stream. The drops break off from the liquid jet 29 at a break off length distance, BL, from the nozzle plate.

It should be appreciated that different mechanical configurations of collector(s), receiver(s), or substrate(s) can be used. For example, in the place of first collector 26, the collection drops enriched with functionalized nanotubes can be deposited and patterned directly on a substrate 1 to form electrical traces, components, or devices, for example, a field effect transistor, electrode, or capacitor. Alternatively, the drops enriched with non-functionalized nanotubes can be selectively deposited onto a substrate, for example, substrate 1 or substrate 2, to form electrical traces, components, or devices, for example, a field effect transistor, electrode, or capacitor. In these example embodiments of the invention, first collector 26, second collector 27, or both can be replaced a receiver or substrate. When this is done, the substrate that replaces first collector 26 can be referred to as a first substrate while the substrate that replaces second collector 27 can be referred to as a second substrate. First substrate, second substrate, or both can be flexible or rigid. Substrate examples include glass, plastics, laminates, or multilayered structures. Typically relative movement between system 28 occurs during printing. First substrate, second substrate, or both can be positioned on a substrate transport that either moves or remains stationary during printing while system 28 either remains stationary or moves, respectively. Alternatively, both the substrate transport and the system 28 can be in a complimentary fashion. As contemplated herein, the substrate and substrate transport themselves are conventional.

Drop forming pulses of the stimulation waveforms 37 are provided by the stimulation controller 23, and are typically voltage pulses sent to the drop formation device(s) 31 of the printhead 22 through electrical connectors, as is well-known in the art of signal transmission. However, other types of pulses, such as optical pulses, can be sent to the drop formation device(s) 31 of printhead 22 to cause collection and recycle drops to be formed at particular nozzles. For example, once formed, the collection drops enriched with functionalized SWNTs travel to and are collected by first collector 26, collector 1, while the recycle drops travel to and are collected by second collector 27, collector 2, as will be described.

Referring to FIGS. 4 and 5, the nanotubes separation system has associated with it, a printhead 22 that is operable to produce from an array of nozzles 30 an array of liquid jets 29. As shown in FIGS. 4 and 5, the arrays 29 and 30 extend into and out of each figure. Associated with each liquid jet 29 are a drop formation device 31 and a drop formation waveform source 34 that supplies a stimulation waveform 37, also called a drop formation waveform, to the drop formation transducer. The drop formation device 31, commonly called a drop formation transducer or a stimulation transducer, can be of any type suitable for creating a perturbation on the liquid jet including, for example, a thermal device, a piezoelectric device, a MEMS actuator, an electrohydrodynamic device, an optical device, an electrostrictive device, and combinations thereof.

In FIG. 5, liquid jet 29 breaks off into drops with a regular period at jet break off location 35, which is a distance BL from the nozzle 30. The distance between a pair of successive drops 36 produced at the fundamental frequency labeled 32 and 33 in FIG. 5 is equal to, or approximates, the wavelength λ of the perturbation on the liquid jet. This sequence of drops breaking from the liquid jet forms a series of drop pairs 36 that includes a drop 32 and a drop 33. Each drop pair includes a first drop and a second drop, one of which is a collection drop and one of which is a recycle drop. The terms first drop and second drop are not intended to indicate a time ordering of the creation of the drops in a drop pair. The frequency of formation of a drop pair 36 is commonly called the drop pair frequency $f_p$, is given by $f_p=f_o/2$ and the corresponding drop pair period is $\tau_p=2\tau_o$.

The creation of the drops is associated with energy pulses supplied by the drop formation device operating at the fundamental frequency $f_o$ that creates drops having the same volume separated by the distance $\lambda$. It is to be understood that although in the example embodiments shown in FIGS. 4 and 5, the first and second drops have essentially the same volume; the first and second drop can have different volumes such that pairs of first and second drops are generated on an average at the drop formation frequency.

Figure 6:
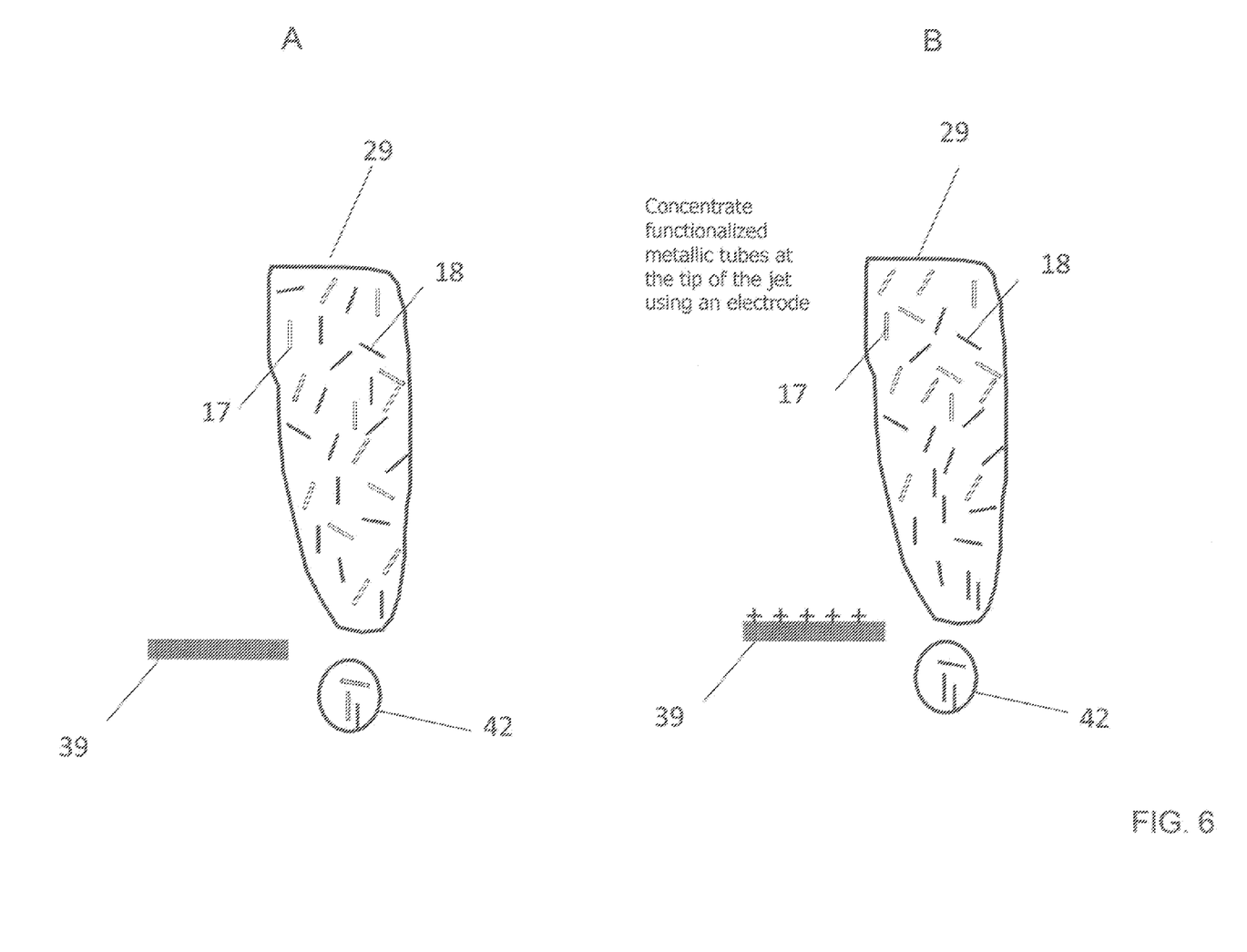

FIG. 5 also shows a charging device 38 including a charging electrode 39 and charging voltage source 40. The charging voltage source 40 supplies a charge electrode waveform 41 which controls the voltage signal applied to the charge electrode. The charge electrode 39 associated with the liquid jet is positioned adjacent to the break off location 35 of the liquid jet 29. If a non-zero voltage is applied to the charge electrode 39, an electric field is produced between the charge electrode and the electrically grounded liquid jet. The capacitive coupling between the charge electrode and the electrically grounded liquid jet attracts functionalized SWNTs carrying opposite charge (by design) to the end of the electrically conductive liquid jet. The liquid jet is grounded through contact with the liquid chamber of the grounded drop generator. This causes the end of the jet to have enrichment in the concentration of functionalized SWNTs 18. This is illustrated in FIG. 6B using, by way of example, a concentration of negatively charged functionalized SWNTs 18 in the end portion of the jet when a positive voltage is applied to the charge electrode 39. If the end portion of the liquid jet breaks off to form a drop while there is a net charge on the end of the liquid jet, the functionalized SWNTs in the end portion of the liquid jet at a concentration higher than the average are trapped in the newly formed drop 42. Thus, in FIG. 6B, the newly formed drop 42 is enriched in negatively charged functionalized SWNTs as compared to the feed solution.

When the voltage level on the charge electrode is changed, the charge induced on the liquid jet changes due to the capacitive coupling between the charge electrode and the liquid jet. Accordingly, the concentration of the functionalized SWNTs on the newly formed drop can be controlled by varying the electric potential on the charge electrode. This is illustrated in FIG. 6A. When the voltage on the charge electrode is zero, the concentration of the functionalized and non-functionalized nanotubes in the newly formed drop 42 corresponds to that of the feed solution.

Referring back to FIGS. 4 and 5, the voltage on the charging electrode 39 (or charging electrodes 39a and 39b) is controlled by a charging voltage source 40 which provides a varying electrical potential in the form of a charge electrode waveform 41 between the charging electrode 44 and the liquid jet 43. In embodiments utilizing the first collection drop selection technique, the charge electrode waveform 41 is usually a two state waveform operating at the drop pair frequency equal to $f_p=f_o/2$, that is at half the fundamental frequency, or equivalently at a drop pair period $\tau_p=2\tau_o$, that is twice the fundamental period. The charge electrode waveform 41 includes a first distinct voltage state and a second distinct voltage state, also referred to as the recycle drop voltage state and the collection drop voltage state, respectively. Each voltage state is usually active for a time interval equal to the fundamental period. In embodiments utilizing the second collection drop selection technique, the charge electrode waveform is a two state waveform operating at the fundamental frequency $f_o$ or equivalently at the fundamental period $\tau_o$, and each voltage state is usually active for a time interval equal to half the fundamental period $\tau_o/2$.

The charging device 38 is synchronized with the drop formation waveform source 34 so that a fixed phase relationship is maintained between the charge electrode waveform produced by the charging voltage source 40 and the clock of the drop formation waveform source. This occurs because the charge electrode waveform period is the same or an integer multiple of the period of the drop formation waveform applied to the drop formation transducer. The phase relationship between drop formation waveforms and the charge electrode waveforms is maintained even though the charge electrode waveform is independent of the image data supplied to the drop formation transducers. As a result, the phase of the break off of drops from the liquid stream, produced by the drop formation waveforms, is phase locked to the charge electrode waveform. For example, in embodiments utilizing the first collection drop selection technique, the drops 32 and 33 shown in FIGS. 4 and 5 are generated one fundamental period $\tau_o$ apart in time so that they have different charge states. Collection drops are formed while the charge electrode is in the collection drop voltage state and recycle drops are formed while the charge electrode is in the recycle drop voltage state so that collection drops 32 are charged to a collection drop charge state and recycle drops 33 are charged to a recycle drop charge state also called a first recycle drop charge state. The first recycle drop charge state is distinct from the collection drop charge state.

Referring back to FIGS. 2, 4, 5, and 6B, the functionalized SWNTs are considered to be negatively charged and the collection drops 32 are considered as having a negative charge. In an alternate example embodiment using the opposite polarity of the two voltage states, the collection drops can be positively charged rather than negatively charged by attaching positively charged functional groups on the type of SWNTs (metallic or semiconducting) to be enriched. Although one type of (either metallic or semiconducting) SWNTs are considered charged, it is possible to attach functional groups of opposite polarities to metallic and semiconducting SWNTs so that the charge electrode voltage can alternate between collection drop voltage state and recycle drop voltage state which are opposite in polarity.

In order to selectively collect collection drops in first collector 26, deflection electrodes 43 and 44 are utilized to attract the collection drops which are then sent to first collector 26. FIG. 4 shows an embodiment in which the deflection electrode 43 attracts collection drops carrying a negative charge traveling along the collection drop path 45. In this embodiment, the collection drop charge state induced on the collection drop of the drop pair is distinct from the recycle drop charge state induced on the recycle drops of the drop pair. The collection drops are highly charged and deflected to first collector 26 while the recycle drops have a relatively low charge (or no charge) and are relatively undeflected and are allowed to reach second collector 27 along the recycle drop path 46. If the recycle drops carry substantial charge with opposite polarity as that of collection drops they are deflected away from the appropriate deflection electrode and collected by second collector 27. As shown in FIG. 4, second collector 27 is positioned to collect recycle drops to facilitate recycling of the ink so that it can be jetted through the print head again. In this manner, the ink can be refined as many times as is desired.

Figure 7:
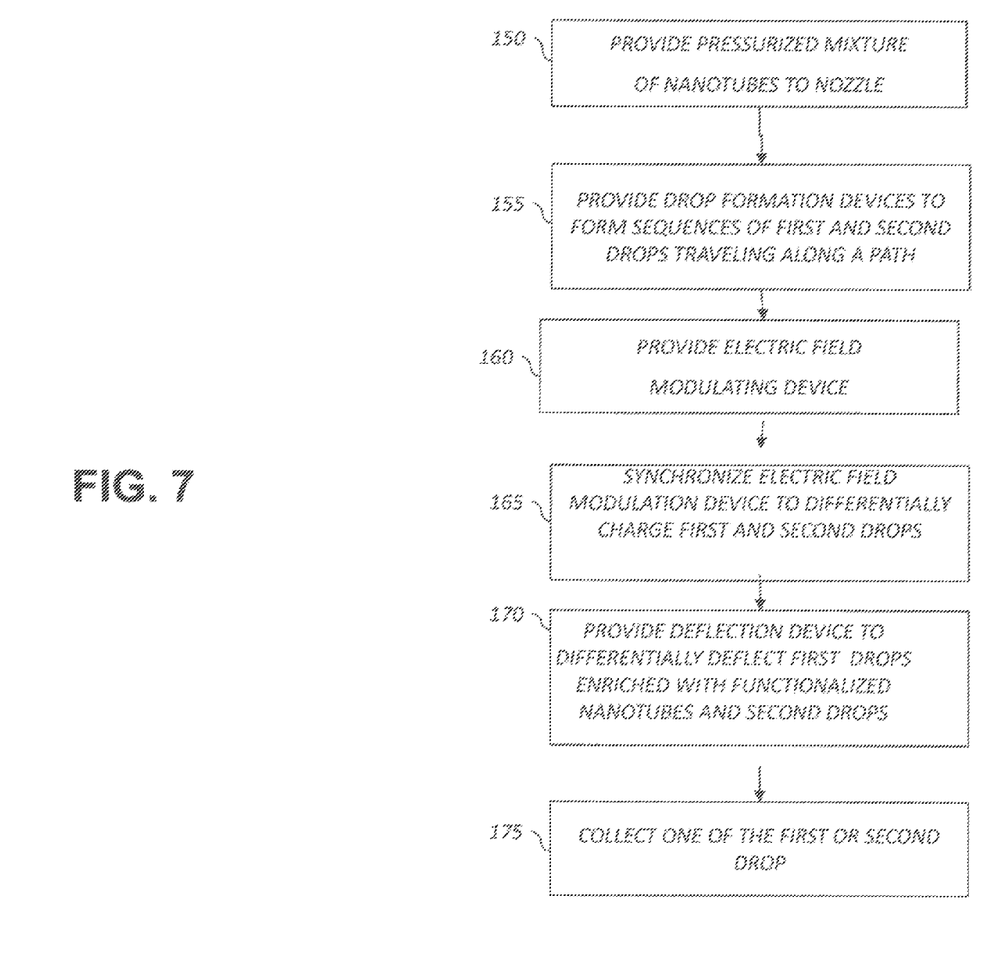

FIG. 7 shows a block diagram outlining the steps to practice the method of sorting SWNTs according to the various embodiments of the invention. Referring to FIG. 7, the method of sorting SWNTs begins with step 150. In step 150, pressurized liquid is provided under a pressure that is sufficient to eject a liquid jet through a linear array of nozzles in a liquid chamber. Step 150 is followed by step 155.

In step 155, the liquid jets are modulated by providing drop formation devices associated with each of the liquid jets with drop formation waveforms that cause portions of the liquid jets to break off into a series of collection drops or recycle drops. The drop formation waveforms control one or more of the break off timing or phase relative to the charging waveform applied to the charge electrode, the drop velocity, and the size of the drop being formed to determine whether a collection drop or a recycle drop is formed. Step 155 is followed by step 160.

In step 160, a common charging device is provided which is associated with the liquid jets. The common charging device includes a charge electrode and a charging voltage source. A charge electrode waveform which includes a first distinct voltage state and a second distinct voltage state is applied to the charging voltage source which results in a varying electrical potential in the vicinity of drop break off from the jets. The first and second voltage states are also called collection drop voltage states and recycle drop voltage states respectively. The charge electrode waveform has a period equal to the minimum time interval between successive collection drops defined as the print period. Step 160 is followed by step 165.

In step 165, the charging device, the drop formation device are synchronized so that the collection drop voltage state is active when collection drops break off from the jets and the recycle drop voltage state is active when recycle drops break off from the jets in all the nozzles in different groups. This produces a collection drop charge state on collection drops and recycle drop charge states on recycle drops. Step 165 is followed by step 170.

In step 170, collection drops are deflected. Collection drops are those drops enriched with functionalized SWNTs. A deflection mechanism includes an electrostatic deflection device which causes the collection to begin traveling along a first trajectory and causes the recycle drop to begin traveling along a second trajectory, the first and second trajectories being different when compared to each other. Step 170 is followed by step 175.

In step 175, drops traveling along one of the first trajectory and the second trajectory are collected by a collector. These drops are collection drops. Drops traveling along the other trajectory are allowed to be collected in a second collector for recycling.

The invention has been described in detail with particular reference to certain preferred embodiments thereof, but it will be understood that variations and modifications can be effected within the scope of the invention.

PARTS LIST

10 Single-Walled Carbon Nanotube (SWNT)
11 Graphene Sheet
12 Roll-Up Vector
13 Armchair Roll-Up Vector
14 Zigzag Roll-Up Vector
15 Unit Vector $a_1$
16 Unit Vector $a_2$
17 Non-Functionalized Semiconducting SWNT
18 Functionalized Metallic SWNT
19 Anionic Functional Group
20 Ink Pressure Regulator
21 Ink Reservoir
22 Printhead or Liquid Ejector
23 Stimulation controller
24 Deflection Mechanism
25 Ink Recycling Unit
26 Collector1
27 Collector2
28 Continuous Inkjet Printing Based SWNT Separation System
29 Liquid Jet
30 Nozzle
31 Drop Formation Device
32 First Drop
33 Second Drop
34 Drop Formation Waveform Source
35 Drop Pair Merge Location
36 Drop Pair
37 Drop Stimulation Waveform
38 Charging Device
39 Charge electrode
39a Second Charge Electrode
39b Optional Symmetric Charge Electrode
40 Charging Voltage Source
41 Charge Electrode Waveform
42 Newly formed Drop
43 Deflection Electrode
44 Optional Deflection Electrode
45 Collection Drop Trajectory
46 Recycle Drop Trajectory

The invention claimed is:

1. A method of separating metallic carbon nanotubes and semiconducting carbon nanotubes comprising:
   providing a source of a mixture of semiconducting carbon nanotubes and metallic carbon nanotubes in a carrier liquid, one of the semiconducting carbon nanotubes and metallic carbon nanotubes being functionalized to carry a charge;
   providing a nozzle in liquid communication with the source;
   pressurizing the source of the mixture to a pressure sufficient to cause a liquid jet of the mixture to be emitted through the nozzle;
   providing a drop formation mechanism;
   modulating the liquid jet using the drop formation mechanism to cause portions of the liquid jet to break off into a first drop and a second drop, the first drop and the second drop traveling along a path;
   providing an electric field modulating device positioned relative to the liquid jet, the electric field modulating device including:
   an electrode; and
   a source of time varying electrical potential between the electrode and the liquid jet that produces a first electrical field and a second electric field;
   providing a deflection device;
   applying the first electric field as the first drop is formed to concentrate the functionalized carbon nanotubes in the first drop;
   applying the second electric field as the second drop is formed; and
   causing the first drop to begin traveling along a second path using the deflection device, wherein the nozzle further comprises a plurality of nozzles in liquid communication with the source.

2. The method of claim 1 further comprising:
   providing a catcher: and
   collecting one of the first drop and the second drop using the catcher.

3. The method of claim 2, where the collected drops are enriched in one of semiconducting carbon nanotubes and metallic carbon nanotubes as compared to the source mixture of semiconducting carbon nanotubes and metallic carbon nanotubes.

4. The method of claim 2, further comprising:
   recycling the liquid of the collected drops back into the source of the mixture; and
   repeating the method of claim 1 to further enrich the concentration of the one of the semiconducting carbon nanotubes and metallic carbon nanotubes.

5. The method of claim 1, wherein the electric field modulating device is common to all of the liquid jets.

6. The method of claim 5, wherein the break off timing of drops formed from the liquid jets emitted from the nozzles of the array is synchronized.

7. The method of claim 1, further comprising:
   providing a substrate; and
   allowing one of the first drop and the second drop to contact the substrate.

* * * * *